(12) United States Patent
Stolz et al.

(10) Patent No.: US 8,563,492 B2
(45) Date of Patent: Oct. 22, 2013

(54) SKIN CLEANSING AGENT WITH PARTICLES CONTAINING HYDROGENATED CASTOR OIL

(75) Inventors: Hermann-Josef Stolz, Bad Munstereifel (DE); Robert Bornicke, Bad Munstereifel (DE); Manfred Matzel, Cologne (DE)

(73) Assignee: Peter Greven Hautschutz GmbH & Co., Bad Munstereifel (DE)

( * ) Notice: Subject to any disclaimer, the term of this patent is extended or adjusted under 35 U.S.C. 154(b) by 0 days.

(21) Appl. No.: 12/529,861

(22) PCT Filed: Mar. 5, 2008

(86) PCT No.: PCT/EP2008/052659
§ 371 (c)(1),
(2), (4) Date: Jun. 10, 2010

(87) PCT Pub. No.: WO2008/107453
PCT Pub. Date: Sep. 12, 2008

(65) Prior Publication Data
US 2011/0046034 A1    Feb. 24, 2011

(30) Foreign Application Priority Data
Mar. 6, 2007    (EP) .................................... 07103635

(51) Int. Cl.
*A61K 8/04* (2006.01)
(52) U.S. Cl.
USPC ............ 510/130; 510/156; 510/426; 510/491
(58) Field of Classification Search
None
See application file for complete search history.

(56) References Cited

U.S. PATENT DOCUMENTS

2003/0180235 A1*  9/2003  Grisoni et al. .................. 424/59

FOREIGN PATENT DOCUMENTS

| DE | 2725924 | 12/1978 |
|---|---|---|
| DE | 4038076 | 6/1992 |
| DE | 10059668 | 6/2002 |
| DE | 10210449 | 9/2003 |
| EP | 0692236 | 1/1996 |
| EP | 0711544 | 5/1996 |
| EP | 1106173 A2 | 6/2001 |
| EP | 1634565 | 3/2006 |
| FR | 2737668 | 2/1997 |
| FR | 2775441 | 9/1999 |
| FR | 2885538 | 11/2006 |
| JP | 2004-189612 | 7/2004 |

OTHER PUBLICATIONS

"Novel wax crystal emulsions and gels" Research Disclosure, Mason Publications, Hampshire, GB, Bd. 511, Nr. 76, Nov. 2006, Seite 1516.
Weleda, "Birken-Dusch-Peeling" Weleda Online 2007, Seiten 1-1, Gefunden im Internet:URL:http://www.weleda.de/Koerperpflege/KopfbisFuss/Duschlotionen/Birkenduschpeeling.html#> [gefunden am Aug. 13, 2007], Accessed May 12, 2010, 1 page.

* cited by examiner

*Primary Examiner* — Necholus Ogden, Jr.
(74) *Attorney, Agent, or Firm* — Woodcock Washburn LLP

(57) ABSTRACT

A skin cleaning agent containing
from 2 to 25% by weight of a cleaning body having a mean grain size of from 100 to 1000 µm and containing at least 50% hydrogenated castor oil;
from 2 to 30% by weight of surfactants;
from 0.1 to 10% by weight of thickeners;
water and optionally further auxiliaries.

8 Claims, 3 Drawing Sheets

SKIN CLEANSING AGENT WITH PARTICLES CONTAINING HYDROGENATED CASTOR OIL

CROSS-REFERENCE TO RELATED APPLICATIONS

This application is the National Stage of International Application No. PCT/EP2008/052659, filed Mar. 5, 2008, which claims the benefit of EP Application No. 07103635.4, filed Mar. 6, 2007, the disclosures of which are incorporated herein by reference in their entirety.

The invention relates to a skin cleaning agent, a cleaning body for said skin cleaning agent, and processes for preparing said cleaning body.

Skin cleaning agents may contain abrasives to improve the cleaning performance that mechanically support the cleaning action of surfactant-like components.

Numerous inorganic and organic abrasives are known and employed, for example, in hand cleaners or peeling preparations.

The abrasives employed first were based on mineral components, such as silica sand or pumice powder. However, there are disadvantages in that silica sand and pumice powders have hard, sharp-edged grains, which results in a poor skin compatibility. Due to their high density, they have a tendency to sedimentation and thus cause the drains to clog.

Further components employed include wood flours. These have an improved skin compatibility and do not sediment in the drains. However, the use of wood flour involves the fundamental risk of allergies against terpene components of the wood. In addition, it is a drawback that wood flour is suspected of being carcinogenic, so that strict safety measures are to be observed when wood flour is prepared and processed.

Further abrasives are obtainable on the basis of polyurethane or polyethylene powder. Regarding their skin compatibility, hardness etc., they are excellently suitable as abrasives. However, they are virtually not biodegradable, so that they are not optimal as regards environment protection and sustainability.

Another group of abrasives are obtainable on the basis of powders of natural substances.

For example, DE 40 38 076 C2 describes shell and kernel flours, especially walnut shell flours.

EP 1 106 173 A2 describes the use of corn cob meal as abrasives.

It is to be considered that a disinfection of the meal employed is necessary in order to avoid a germ contamination of the products. The above mentioned EP 1 106 173 describes a bleaching method for natural flours that simultaneously kills any germs that might be present. While the use of such natural flours is highly suitable under sustainability aspects in principle, the properties of such flours are still not optimal.

The degree of contamination in the various workplaces in the industry is decreasing due to the increased demands for working safety and hygiene. Therefore, there is a demand, not least from professional dermatologists, for products that are more skin-friendly. Above all, the abrasives are in the focus here.

US 2003/0180235 describes processes for preparing microparticles in which the microparticles may contain low proportions of castor oil.

EP 0 711 544 A2 describes a dentifrice composition containing agar-coated capsules filled with medicinally active substances. A Comparative Example shows the use of capsules containing castor oil and sodium copper chlorophyllin.

DE 100 59 668 A1 describes nanoparticulate waxes having a mean particle diameter of from 5 to 500 nm. Due to their low size, they do not act as cleaning bodies.

There is still a need for skin cleaning agents that offer a good cleaning performance while having improved skin-preserving properties. It is the object of the present invention to provide a cleaning body and a skin cleaning agent containing said cleaning body that overcome the mentioned drawbacks of the prior art, especially exhibit a high skin compatibility.

This object is achieved by a skin cleaning agent containing
- from 2 to 25% by weight of a cleaning body having a mean grain size of from 100 to 1000 μm and containing hydrogenated castor oil;
- from 2 to 30% by weight of surfactants;
- from 0.1 to 10% by weight of thickeners;
- water and optionally further auxiliaries.

According to the invention, cleaning bodies containing castor oil, i.e., the oil obtained from *Ricinus communis* seeds, which is subsequently hydrogenated at least partially, are employed.

The cleaning body according to the invention contains at least 50% castor oil, preferably at least 70% castor oil and most preferably at least 90% by weight castor oil.

Preferably, the cleaning body does not contain any sodium copper chlorophyllin.

The degree of hydrogenation can be established by determining the iodine number. Castor oils having an iodine number of from 0 to 20 mg of $I_2$/100 g have proven particularly suitable. The content of cleaning bodies in the skin cleaning agent is preferably at least 3% by weight, more preferably at least 5% by weight, even more preferably at least 6% by weight, or at least 7% by weight.

Surprisingly, the cleaning bodies according to the invention show a stain-releasing and stain-absorbing behavior. When the cleaning agent according to the invention is employed, dirt particles form some kind of coat around the cleaning bodies according to the invention. In this way, a good cleaning effect is achieved.

The cleaning bodies according to the invention have no or only little abrasive effect; therefore, the cleaning agent according to the invention is especially skin-preserving.

In principle, the cleaning bodies may contain further substances, especially waxes, in addition to the hydrogenated castor oil. Particularly suitable are paraffin waxes, carnauba waxes, candelilla waxes, polyethylene waxes, oxidized polyethylene waxes or mixtures thereof. It is to be taken care that those waxes are selected that have a melting range above 40° C., preferably above 80° C.

Surprisingly, it is found that the cleaning bodies are stable even in the presence of solvents, such as dibasic ester (DBE). Thus, the cleaning bodies may also be employed in special products, such as paint cleaners.

Surprisingly, it is found that the cleaning bodies employed will not dissolve in the skin cleaning agent despite the presence of the surfactants.

Surprisingly, it is also found that the cleaning bodies employed according to the invention remain stable under the usual shipping and storing conditions.

As surfactants for use in the skin cleaning agent, in particular, non-ionic, zwitterionic and anionic surfactants have proven suitable, for example, ether sulfates, betaines, alkyl sulfonates, succinates, alkylpolyglycosides, protein/fatty acid condensates, polyglycol ethers, soaps and mixtures thereof. The choice of appropriate surfactants is familiar to the skilled person.

As thickeners, in particular, bentonites, xanthan gums, acrylates, alginates, cellulose ethers, carrageenan and mixtures thereof are suitable.

Usually, the skin cleaning agent according to the invention may contain one or more of the following usual additives:

refatting agents colorants perfumes titanium dioxide buffer substances preservatives liquid paraffins glycerol antioxidants The flowability of the skin cleaning agent can be adjusted through the content of thickeners and the content of cleaning bodies. With low contents of thickeners and cleaning bodies, flowable pastes are obtained. With relatively high contents, solid cleaning pastes are obtained, as often employed, for example, for hand cleaning.

Surprisingly, the product according to the invention is rather skin-friendly since the castor oil employed has additional properties as a refatting agent and emulsifier.

Preferably, the product is in the form of an aqueous suspension. An oil-in-water emulsion is less preferred.

The cleaning effect of the cleaning bodies can be influenced by the grain size and the preparation process. In principle, larger cleaning bodies have a stronger effect.

The cleaning body according to the invention is preferably prepared by a process in which the hydrogenated castor oil is molten, optionally with the addition of further materials, especially further waxes, followed by dispersing the melt into droplets or spraying it.

When sprayed, the molten wax mixture is sprayed under high pressure through nozzles. The grain size distribution curve has a relatively broad base. Further, the droplets have less uniform shapes from coalescence.

Products dispersed into droplets have a substantially narrower grain size distribution curve. The products are uniformly round and have a lesser tendency to agglomerate because of the wider drop cone. Droplet-generating devices use a rotating disk instead of the spraying nozzles. It bears defined bores that determine the diameter of the particles.

The irregular bodies have better mechanical cleaning properties, but a poorer skin compatibility due to this fact.

In principle, it is also possible to mix the cleaning bodies according to the invention that are based on hydrogenated castor oil with abrasives, for example, polyurethane abrasive bodies, and to employ the mixture in skin cleaning agents.

The invention also relates to a cleaning body for cosmetic preparations having a mean particle size of from 100 to 1000 μm and containing hydrogenated castor oil, and a process for preparing said cleaning bodies, comprising the steps of melting hydrogenated castor oil, optionally together with further substances, followed by dispersing the melt obtained into droplets or spraying it.

The invention further relates to the use of cleaning bodies having a mean grain size of from 100 to 1000 μm and containing hydrogenated castor oil for the preparation of cosmetics, especially skin cleaning agents.

In principle, the waxes may also contain cosmetically active ingredients. By combining different waxes, the properties of the cleaning bodies can be readily adjusted.

| Wax | Dropping point [° C.] DIN 51801 | Penetration [0.1 mm] DIN 51579 |
|---|---|---|
| Carnauba wax | 81-86 | <1 |
| Candelilla wax | 68-73 | <2 |
| Paraffin wax (hard) | 105-120 | 1-4 |
| Paraffin wax | 56-60 | 160-210 |
| Polyethylene wax | 105-115 | 2-5 |
| Oxidized polyethylene wax | 101-109 | <6 |
| Hydrogenated castor oil | 84-88 | 3-6 |

Cleaning bodies according to the invention can also be obtained if a wax having similar properties as hydrogenated castor oil, especially in terms of hardness and melting range, is employed instead of said hydrogenated or partially hydrogenated castor oil.

Preferably, the deviation in the dropping point and penetration of other waxes from those of the hydrogenated castor oil employable according to the invention is not greater than 20%.

The invention is further illustrated by the following Examples.

EXAMPLE 1

A skin cleaning agent having the following composition was prepared:

| INCI EU | Proportion in % |
|---|---|
| Sodium C12-18 alkylsulfate | 15.000000 |
| Aqua | 15.000000 |
| Paraffinum liquidum | 18.000000 |
| Aqua | 16.500000 |
| Sodium C12-15 pareth sulfate | 8.750000 |
| Aqua | 3.750000 |
| Hydrogenated castor oil | 10.000000 |
| Aqua | 3.000000 |
| Sodium xylenesulfonate | 2.000000 |
| Glycerol | 3.00000 |
| Oleic acid | 1.500000 |
| Sodium chloride | 1.200000 |
| Coco glucoside | 0.330000 |
| Glyceryl oleate | 0.330000 |
| Aqua | 0.340000 |
| Phenoxyethanol | 0.560000 |
| Butylparaben | 0.060000 |
| Ethylparaben | 0.060000 |
| Methylparaben | 0.060000 |
| Propylparaben | 0.060000 |
| Titanium dioxide | 0.200000 |
| Perfume | 0.200000 |
| Citric acid | 0.100000 |

Figure 1:
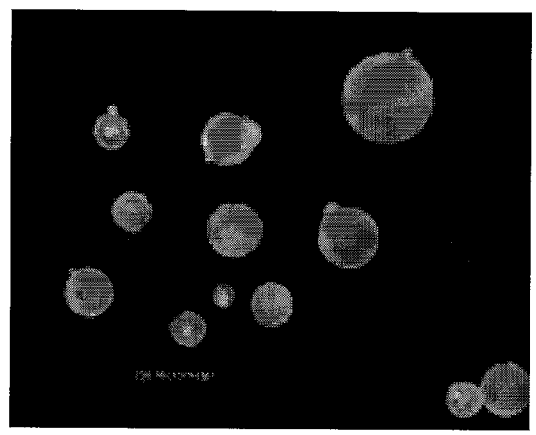
FIG. 1 shows cleaning bodies as obtained from the spraying method.
Figure 2:
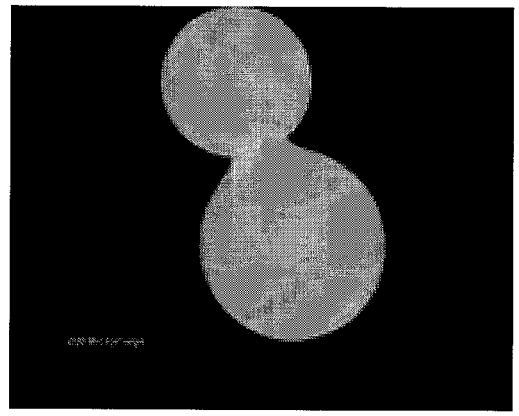
FIG. 2 shows cleaning bodies as obtained from the dispersion-into-droplets method.
Figure 3:
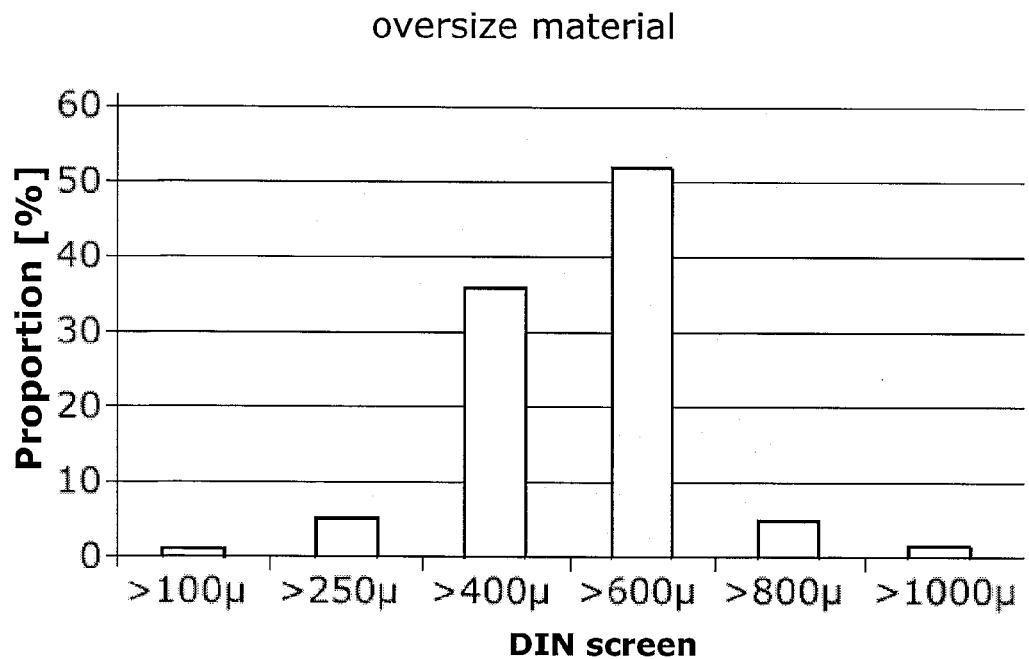
FIG. 3 shows the grain size distribution of the cleaning bodies according to Example 1.

The hydrogenated castor oil employed has a grain size distribution according to FIG. 3.

A relatively solid skin cleaning paste was obtained that was suitable for removing heavy dirt, such as soot, grease, lubricating oils. It was found that the cleaning bodies remain stable over an extended period of time, even under elevated temperature conditions as occur, for example, during shipping or storage in the summer.

EXAMPLE 2

| INCI EU | Proportion in % |
| --- | --- |
| Aqua | 60.5065 |
| Sodium C12-15 pareth sulfate | 8.00 |
| Hydrogenated castor oil (as in Example 1) | 18.00 |
| Sodium C12-18 alkylsulfate | 5.00 |
| Potassium cocoyl hydrolyzed collagen | 1.00 |
| Glyceryl ricinoleate | 2.00 |
| PEG-7 glyceryl cocoate | 2.00 |
| Bentonite | 2.50 |
| Titanium dioxide | 0.60 |
| Citric acid | 0.25 |
| Perfume | 0.10 |
| 2-Bromo-2-nitropropane-1,3-diol | 0.036 |
| CI 13015 | 0.002500 |
| CI 15510 | 0.002500 |
| CI 61570 | 0.002500 |

Example 2 is a flowable paste that can be used with dispensers and is considered for the heaviest grease and grime. The effective combination of surfactants becomes substantially more skin-compatible all in all by using protein/fatty acid condensates. The cleaning action is supported by the abrasive, which has a high dirt binding capacity just for greases and lubricating oils. Refatting substances lower the risk of skin irritations.

EXAMPLE 3

| INCI EU | Proportion in % |
| --- | --- |
| Aqua | 71.166 |
| Sodium laureth sulfate | 14.28 |
| Wax mixture: | 5 |
| 85% hydrogenated castor oil | |
| 12% paraffin | |
| 3% carnauba wax | |
| Cocamidopropylbetaine | 4.45 |
| PEG-7 glyceryl cocoate | 2.00 |
| Bentonite | 1.80 |
| Citric acid | 0.55 |
| Titanium dioxide | 0.50 |
| Perfume | 0.10 |
| 2-Bromo-2-nitropropane-1,3-diol | 0.054 |
| Xanthan gum | 0.10 |

The mixture has a dropping point of 78° C. and a penetration of 214 at 0.1 mm.

Example 3 is also a flowable paste; it is used for a medium degree of contamination of the skin. The surfactant combination shows a significantly reduced cleaning power as compared to Example 2. PEG-7 glyceryl cocoate also has a refatting activity in addition to its excellent emulsifying and foaming properties. The pH is matched to that of the skin.

EXAMPLE 4

| INCI EU | Proportion in % |
| --- | --- |
| Aqua | 27.002 |
| Hydrogenated castor oil (as in Example 1) | 25.00 |
| Sodium C12-18 alkylsulfate | 23.73 |
| Paraffinum liquidum | 18.00 |
| Potassium cocoyl hydrolyzed collagen | 2.00 |
| Citric acid | 2.00 |
| Isodeceth-7 | 1.00 |
| Oleic acid | 1.00 |
| Perfume | 0.20 |
| 2-Bromo-2-nitropropane-1,3-diol | 0.018 |
| Titanium dioxide | 0.050 |

Example 4 is a solid to paste-like hand cleaning cream. It is designed for the removal of the heaviest grease and grime, such as soot, greases, bitumen etc. The high cleaning power is due to the content of paraffin oil (DAB) on the one hand and the effective combination of surfactants on the other. Despite of the relatively high proportion of paraffin, the cleaning agent remains stable for months.

EXAMPLE 5

| INCI EU | Proportion in % |
| --- | --- |
| Dimethyl glutarate | 27.0 |
| Dimethyl succinate | 8.3 |
| Dimethyl adipate | 6.2 |
| Aqua | 11.0 |
| Disodium laureth sulfosuccinate | 9.2 |
| Aqua | 13.2 |
| Hydrogenated castor oil (as in Example 1) | 11.5 |
| Ethylhexyl stearate | 4.6 |
| Paraffinum liquidum | 4.6 |
| Stearalkonium bentonite | 3.0 |
| Bentonite | 1.0 |
| Perfume | 0.2 |
| Titanium dioxide | 0.2 |
| | 100 |

The exemplary formulation 5 represents a paste-like special hand cleaning agent for the removal of strongly adhering dirt, such as bitumen, paints or adhesives. This strong cleaning effect is achieved by the use of a dibasic ester. Succinate is employed as a skin-compatible surfactant. Despite this ingredient, the cleaning agent remains stable.

EXAMPLE 6

The abrasive effect of the cleaning bodies according to the invention was analyzed. As a testing method, the Miller method standardized as ASTM-G75-01 was applied. This method enables a standardized measurement of the abrasiveness of particle-containing fluid/solid mixtures. Instead of the metallic standard test specimen as employed in the standard, a block of LDPE plastic was employed. The testing time was set at 10 min. In order to obtain a paste-like mass, the cleaning bodies were slurried with water at a ratio of 1:1.

Figure 4:
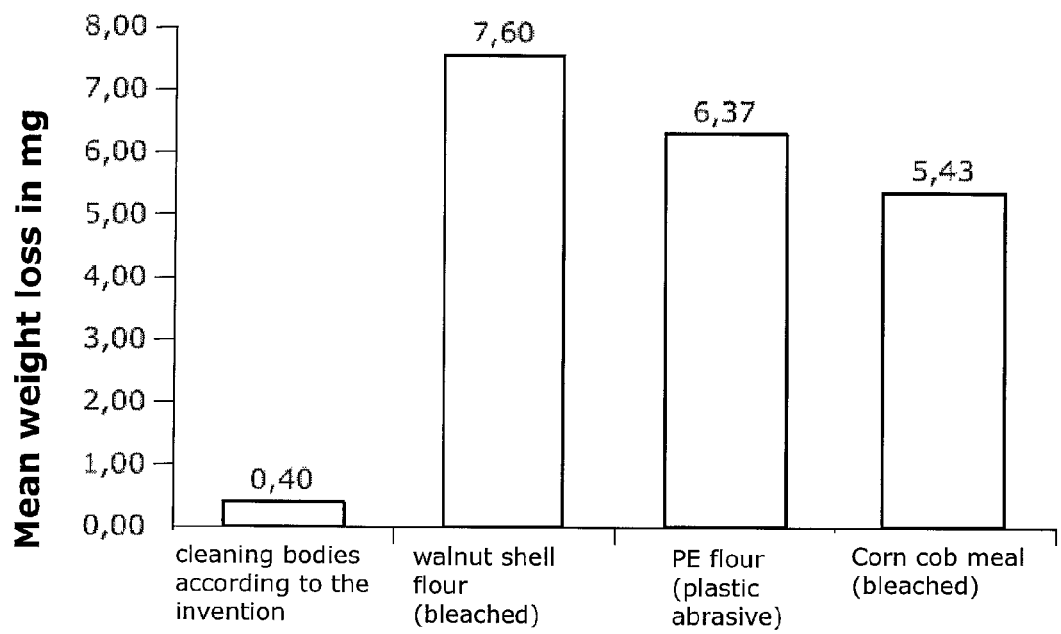
FIG. 4 shows a comparison of the abrasion effect of different cleaning agents.

FIG. 4 shows the abrasive effect as compared to bleached walnut shell flour, polyethylene flour and corn cob meal.

EXAMPLE 7

To demonstrate the dirt binding activity, the abrasive bodies according to the invention were admixed with a standard dirt:

| | |
|---|---|
| 54.00% | Paraffinum liquidum |
| 18.10% | Petroleum jelly |
| 3.60% | Graphite |
| 18.10% | Wool wax |
| 5.40% | Flame soot |
| 0.80% | Ferric oxide | and subsequently rinsed with water in a screen.

Figure 5A:
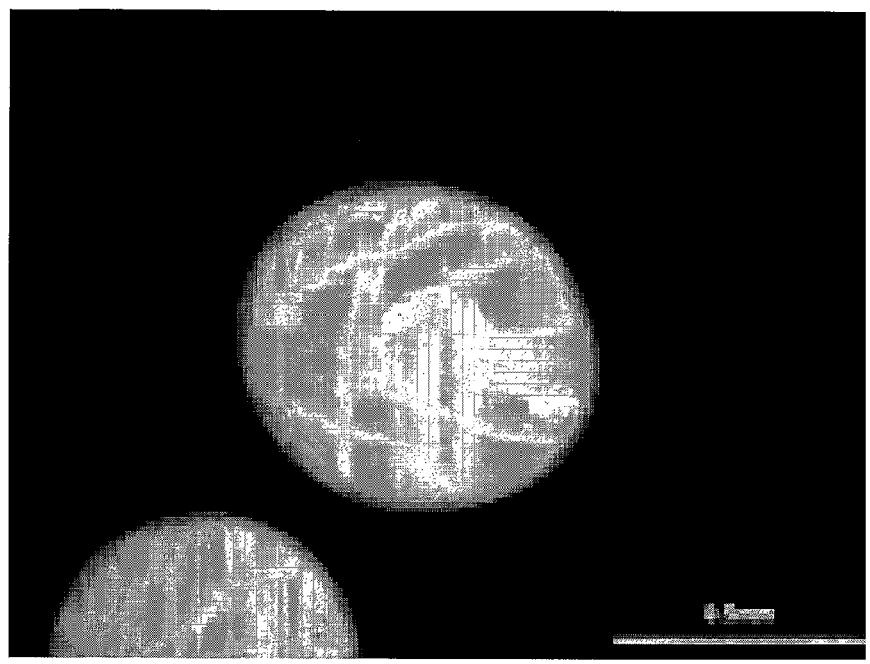
FIGS. 5a and 5b show optical micrographs of the cleaning bodies before and after contact with dirt.
Figure 5B:
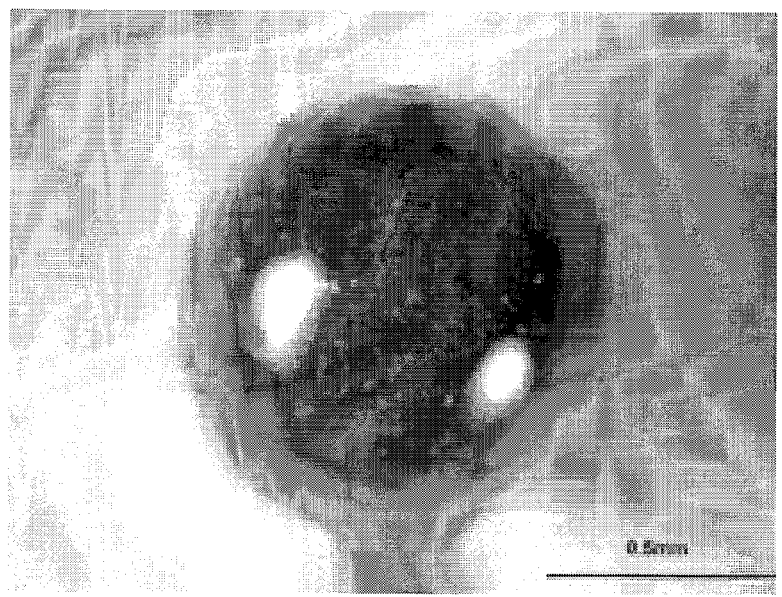

FIG. 5a shows the cleaning bodies before the treatment, while FIG. 5b shows them after the treatment. The binding of the dirt is clearly visible.

EXAMPLE 8

In a skin compatibility test, the effect on the skin was examined for a seven day application. What was examined was the effect of a treatment with
a) water
b) a usual dishwashing detergent
c) cleaning bodies according to the invention suspended in the dishwashing detergent according to b)
d) suspended in the dishwashing detergent according to b) with bleached walnut shell flour.

With the corresponding treating agent, washing was performed daily. The effect was examined both in a group of atopics and in the group of non-atopics.

It was found that the TEWL (transepidermal water loss) decreases in the group of atopics. With treatment c), the TEWL decreases from 6 to 3.2, while it increases to 6.4 when treatment d) is employed.

In corneometry, the moisture content of the skin increases in the atopics group and decreases when treated with walnut shell flour.

The erythema is slightly reduced by the treatment in all groups. No relevant differences are found in the pH, skin fat and skin elasticity.

The invention claimed is:

1. A skin cleaning agent containing
   from 2 to 25% by weight of solid cleaning bodies having a mean grain size of from 100 to 1000 μm and containing at least 50% by weight of hydrogenated castor oil;
   from 2 to 30% by weight of an ether sulfate, alkyl sulfate, alkyl sulfonate, or sulfosuccinate surfactant, or a mixture there of;
   from 0.1 to 10% by weight of thickeners;
   water and optionally further auxiliaries;
   wherein said solid cleaning bodies resist dissolution in the skin cleaning agent.

2. The skin cleaning agent according to claim 1, wherein said castor oil is completely or partially hydrogenated.

3. The skin cleaning agent according to claim 1, wherein said cleaning bodies additionally contain paraffin waxes, carnauba waxes, candelilla waxes, polyethylene waxes, oxidized polyethylene waxes or mixtures thereof having a melting point of above 40° C.

4. The skin cleaning agent according to claim 1, wherein said thickener is selected from bentonites, xanthan gums, acrylates, alginates, cellulose ethers, carrageenan and mixtures thereof.

5. The skin cleaning agent according to claim 1, characterized by additionally containing one or more of the following substances:
   refatting agents;
   colorants;
   perfumes;
   titanium dioxide;
   buffer substances;
   preservatives;
   liquid paraffins;
   glycerol;
   antioxidants;
   abrasives.

6. Cleaning bodies for cosmetic preparations, including skin cleaning agents, having a mean grain size of from 100 to 1000 μm and containing at least 50% by weight of hydrogenated castor oil, wherein said solid cleaning bodies resist dissolution in a skin cleaning agent containing:
   from 2 to 25% by weight of said cleaning bodies;
   from 2 to 30% by weight of an ether sulfate, alkyl sulfate, alkyl sulfonate, or sulfosuccinate surfactant, or a mixture there of;
   from 0.1 to 10% by weight of thickeners;
   water and optionally further auxiliaries.

7. A process for preparing the cleaning bodies according to claim 6, comprising the steps of:
   melting hydrogenated castor oil, optionally together with further waxes;
   dispersing the melt into droplets or spraying it.

8. A method of preparing the skin cleaning agent of claim 1, comprising mixing the cleaning bodies having a mean grain size of from 100 to 1000 μm and containing at least 50% by weight of hydrogenated castor oil with the surfactants, thickeners, water, and optional auxiliary.

* * * * *

UNITED STATES PATENT AND TRADEMARK OFFICE
CERTIFICATE OF CORRECTION

PATENT NO. : 8,563,492 B2
APPLICATION NO. : 12/529861
DATED : October 22, 2013
INVENTOR(S) : Stolz et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 282 days.

Signed and Sealed this
Fifteenth Day of September, 2015

Michelle K. Lee
*Director of the United States Patent and Trademark Office*